(12) United States Patent
Hipp (10) Patent No.: US 8,459,050 B2
(45) Date of Patent: Jun. 11, 2013

(54) INJECTION DEVICE

(75) Inventor: Richard Hipp, Wasmuthhausen Maroldsweisach (DE)

(73) Assignee: DeBe Tek GmbH, Wasmuthhausen Maroldsweisach (DE)

( * ) Notice: Subject to any disclaimer, the term of this patent is extended or adjusted under 35 U.S.C. 154(b) by 363 days.

(21) Appl. No.: 12/821,905

(22) Filed: Jun. 23, 2010

(65) Prior Publication Data
US 2010/0326117 A1 Dec. 30, 2010

(30) Foreign Application Priority Data

Jun. 24, 2009 (DE) .................. 20 2009 008 674 U
May 14, 2010 (DE) .................. 10 2010 020 508

(51) Int. Cl.
*F25B 1/00* (2006.01)

(52) U.S. Cl.
USPC .................................. 62/115; 62/292; 62/500

(58) Field of Classification Search
USPC ................. 62/292, 500, 259.1, 115; 239/164, 239/174; 60/39.71, 39.724
See application file for complete search history.

*Primary Examiner* — Mohammad M Ali
(74) *Attorney, Agent, or Firm* — Workman Nydegger (57) ABSTRACT

The invention relates to an injection device for injecting an injection medium into a volumetric flow of a line system. The injection device comprises a housing with at least one first compartment which is set up to receive an injection medium, and at least one second compartment which is spatially separated from the first compartment, both compartments having an injection unit.

12 Claims, 5 Drawing Sheets

INJECTION DEVICE

BACKGROUND OF THE INVENTION

1. Field of the Invention

The invention relates to an injection device for injecting an injection medium into a volumetric flow of a line system or into a volume, in particular of a ventilation and/or venting system.

2. Background and Relevant Art

Injection devices of this type are used, for example, in order to disinfect or distribute aroma to line systems, such as, for example, in air conditioning systems and the like, or to charge said line systems with an injection medium.

EP 0 687 869 A2 discloses a device of this type. In said device, disinfection is achieved by the air flowing in the line system initially being ionized and subsequently being mixed with a disinfectant. However, disinfection in this manner is comparatively complicated.

BRIEF SUMMARY OF THE INVENTION

On the basis thereof, it is an object of the invention to provide an injection device with which a line system or volume can in particular be disinfected comparatively simply and nevertheless effectively. Furthermore, an injection device which can be used particularly flexibly is to be provided.

This object is achieved by the features of the independent patent claims. Refinements emerge from the dependent patent claims.

According to claim 1, an injection device is designed (or: is provided which is designed) to inject at least one injection medium into a volumetric flow of a line system or into a preferably closed volume. In this case, the injection medium may be in gaseous, liquid or solid form. The at least one injection medium is preferably a disinfection medium and/or aroma medium and/or the injection device is a disinfection and aroma distributor for disinfecting and distributing aroma. The line system may be in particular a ventilation and/or venting system, such as, for example, an air conditioning system, a room or premises. However, any other volumes and line systems, in particular pipeline systems, are also suitable. In particular, the injection device may also be used in greenhouses for applying plant protection agents, growth-promoting agents and the like. Further fields of use of the injection device are conceivable, such as, for example, in the food industry or for applying liquid media, in particular oils, lubricants, water, etc.

The injection device comprises a housing with at least one first compartment (or: a first chamber). The first compartment is designed and set up to indirectly or directly accommodate at least one of the at least one injection medium. In this case, directly and indirectly to accommodate is intended to mean that the injection medium can be located directly in the compartment or that the injection medium can be accommodated in a separate container which is located in the first compartment or can be inserted interchangeably into the first compartment.

The injection device furthermore comprises at least one second compartment which is spatially separated from the first compartment or occupies a different spatial region. Each second compartment has at least one injection unit for injecting at least one of the at least one injection medium into the volumetric flow of the line system or into the volume. The at least one first compartment is preferably arranged spatially below the at least one second compartment. Electronic components, such as control systems and the like, may also be accommodated in the at least one second compartment, or in at least one further third compartment.

The housing may be a lectern-like, preferably closed, in particular lockable, upright housing. In order to prevent unauthorized access to the components accommodated in the first and second compartments, the housing may have a door or, if appropriate, a door for each compartment, which is lockable, for example using a key-lock system or a different locking or catch system. If the housing has one or more doors, the interior of the housing is a space which is locked per se when the door is closed or when the doors are closed. In order to avoid a build up of heat in the closed housing, which could possibly lead to damage of the components accommodated therein, the housing may have a cooling device, in particular an aeration system, in particular a ventilation and venting system, and, in a simple refinement, one or more aeration slots or aeration grills. The aeration system may be designed to be active or passive.

In the case of an active aeration system, a cooling device can be provided for actively cooling components located in the housing, in particular electronic components. The cooling device may be designed in such a manner that a cooling medium, in particular a gaseous cooling medium, preferably air, or a liquid cooling medium is guided in a suitable manner in or through the housing such that the components can be optimally cooled. For example, the cooling device may have one or more fans which generate a coolant stream by means of which components which generate waste heat or are to be cooled can be cooled. In this situation, ambient air, for example, may be used as the cooling medium. As an alternative or in addition, the cooling device may comprise active cooling elements, such as evaporators or Peltier elements and the like.

In the case of a passive aeration system, aeration slots or grills may be arranged in or on the housing in such a manner that a cooling air stream is produced by the heat or waste heat generated in the housing. The aeration slots or grills are advantageously designed and arranged in such a manner that the components to be cooled are acted upon to a sufficient extent with a cooling airstream.

The housing may furthermore have a separate, third compartment which is designed in particular in the manner of a storage compartment which is preferably separate from the first and second compartments. The third compartment may be designed to accommodate additional components, in particular electronic components, or other utensils. The third compartment is advantageously provided with a lockable door or flap. In the case of a lectern-like housing, the third compartment may be arranged in an upper housing region, preferably with an opening upwards or obliquely upwards, in which case a preferably lockable, upwardly opening or raisable door or flap may be provided for the opening. The door or flap may have one or more, in particular digital, display elements or displays, one or more control panels, switching elements, command buttons or other electronic elements. However, depending on requirements, the above-mentioned components and elements may also be arranged at different locations on the housing. The third compartment may also be designed as a preferably forwardly opening drawer or as a pull-out tray.

The injection device is structurally simple and may be used flexibly, in particular for a multiplicity of different injection media. Suitable injection media include, in particular, disinfectants, aroma substances, aqueous solutions mixed with disinfectants and/or aroma substances etc. and any combinations thereof.

As already mentioned, the injection medium may be accommodated indirectly in the first compartment. For example, the injection medium may be accommodated in a separate container, in particular interchangeable container, or canister. Using interchangeable containers, it is possible for the injection device to be equipped, filled and refilled in a particularly flexible manner with one or more injection media. A plurality of interchangeable containers having identical or different injection media may be provided or connected, and therefore even relatively large quantities of injection medium can be stored. Each of the interchangeable containers connected to the injection device may be accommodated in a separate first compartment. However, it is also possible for all or more than one of the interchangeable containers to be accommodated in a common first compartment.

In order to establish the level of the interchangeable container or of the interchangeable containers, said interchangeable container/interchangeable containers may comprise a level display. The level display may be provided separately on each interchangeable container. It is also possible for the injection device to have a central level display, for example a digital display, on which the levels of all of the interchangeable containers connected or installed can be displayed. The digital display may be provided, for example, on or integrally with a door or flap.

The interchangeable container may be a pressure-operated interchangeable container which can be acted upon with a positive pressure in order to remove injection medium. As an alternative, in particular when pumps are used, a canister or the like may be used as the interchangeable container.

According to one refinement, the at least one first compartment and/or the at least one second compartment is designed to be movable, in particular to be able to be pulled out, relative to the housing in the manner of a drawer. In this manner, an interchangeable container located in the compartment can in particular be replaced or removed in a simple manner by the respective first compartment being pulled out in the manner of a drawer, and therefore the interchangeable container located therein being easily accessible and replaceable. Furthermore, if there is a second compartment which can be pulled out, said compartment or the injection units accommodated therein can be replaced or maintained in a simple manner.

Each injection unit may comprise at least one pump and/or a compressor which is/are designed to inject the injection medium in the volumetric flow, preferably via an injection head. With a pump, the injection medium may be, for example, removed from the interchangeable container and supplied to the injection head, and the pressure required for the injection can be produced by the pump itself. As an addition, in this refinement, a compressor may also be used to generate the required pressure. In particular if pressure-operated interchangeable containers are used, the latter can be pressurized by the compressor or the compressors in order, for example, to supply the injection medium to the injection head at the positive pressure required for the injection. It should be pointed out that the compressor and/or the pump may be integrated in the interchangeable container, it being possible in this case for the injection unit to comprise one or more electronic control units for controlling the compressor and/or the pump. The in particular electronic control unit(s) or other in particular electronic components, such as pressure capsules, timers, temperature sensors, cooling elements etc. may be accommodated in the first, second and/or third compartment.

The injection medium may be injected continuously. However, a discontinuous injection is also possible. For this purpose, the injection device may have a trigger device, such as, for example, a timer, which is designed to trigger the injection of the at least one injection medium in accordance with predetermined time intervals. For example, the injection medium may be injected for 20 or 30 seconds in each case at intervals of 60 minutes or for 10 seconds at an interval of 15 or 20 minutes. The trigger device can be used to adapt the injection of the injection medium to the particular requirements and circumstances of the line system, such as length, diameter, volumetric flow, etc. The trigger device is preferably designed in such a manner that the triggering can be set or adjusted specifically, which means that waiting periods and injection periods can be set and changed as desired.

In one refinement, the injection unit is designed in such a manner that the at least one injection medium is injected or can be injected at a positive pressure of 1 to 6 bar, preferably 2 to 3 bar. In particular for such pressures and those with regard to the switching cycles occurring upon triggering, solenoid valves have proven particularly advantageous in order to control the injection of the injection medium or of the injection media. In particular when the solenoid valves which can be switched precisely and comparatively rapidly are used, it is possible for one injection unit to be connected to a plurality of interchangeable containers in order, for example, to inject different injector media simultaneously or following one another immediately or shortly after one another, and also at different positive pressures, depending on requirements.

To connect the interchangeable containers to the injection unit and the injection unit to the at least one injection head, use may be made of any pipelines, hoses and the like which are resistant to the respectively used injection media. Pipe connections or hose connections between the abovementioned components can be produced or released in particularly simple manner if plug-in couplings and/or rapid-action couplings are used at least in part.

The injection device may comprise at least one injection head for injecting at least one of the injection media into the line system or the volume. The at least one injection head may be designed in such a manner that the latter can be at least partially placed into the flow path of the line system, preferably transversely with respect to the flow direction. Furthermore, the injection head can be adjusted, preferably in the length thereof, and therefore the injection device can be used for a multiplicity of differently dimensioned line systems. In particular, it is easily possible, using the abovementioned development, both to connect the injection device to line systems which already exist and to integrate said injection device into line systems to be newly installed. In the event of installation on line systems which already exist, walls of the line system may be provided with bores, corresponding to the outside diameter of the injection head, for example in the region of approx. 20 mm. The injection head or the injection heads may be attached to said bores, in particular retrofitted thereto, and, depending on requirements, may be connected to the injection device, preferably via hoses with rapid-action couplings.

A comparatively simple connection of an injection head is possible if corresponding connections are attached to the outside of the housing, preferably at easily accessible locations, such as at the top, at the front and/or side. The connections may have securing devices, such as catches, which prevent unauthorized release or connection of an injection head.

The injection head may be designed to inject the injection medium or the injection media in gaseous form or in the form of liquid or solid aerosols into the volumetric flow. In this case, the injection medium itself may be present in gaseous, liquid or solid form, in particular powder form. The injection medium may comprise a disinfectant, a fragrance and/or other agents, the addition of which to the volumetric flow is desirable. The injection medium may be dispensed into the volumetric flow via nozzles, in particular hollow cone nozzles. The nozzles preferably have a filter, in particular an integrated filter. Furthermore, a pressure capsule and/or a valve may be provided in order to activate and/or to block the nozzle(s), for example when switching the injection device on or off. With such precautions, the respective injection medium can be injected with a high degree of accuracy and in the respectively desired concentration into the volumetric flow.

Overall, it has been shown that the injection device is of comparatively simple construction and can be used in a flexible manner and the injection medium can nevertheless be injected effectively.

In another version of the invention which can be claimed independently or else in combination with the other versions and embodiments, the injection device which is designed for injecting at least one injection medium into a volumetric flow of a line system, in particular a ventilation and/or venting system, or into a preferably closed volume, comprises an injection head which can be or is at least partially placed into the flow path of the line system, preferably transversely with respect to the direction of flow and is intended for injecting at least one of the injection media into the line system, wherein the injection head can be adjusted preferably in the length thereof which is located within the line system and/or running in the direction transversely with respect to the direction of flow and/or in the axial position thereof within the line system.

The injection head has an injector nozzle, in particular a hollow cone nozzle, in particular with a filter, in particular an integrated filter, wherein the injector nozzle has in particular a nozzle housing which is dome-shaped or curved on the outside and has an internal, conically tapering channel which leads into an outlet opening of the injector nozzle for the injection medium. Furthermore, the injection head preferably has a supply tube with a front end which projects into the line of the line system, and with a rear end, wherein the injector nozzle is preferably connected, preferably releasably, at the front end of the supply tube, in particular by means of a screw connecting piece which is or can be screwed to the supply tube by means of corresponding threads. In a preferred refinement, the supply tube is guided in an axially movable manner axially along the longitudinal direction thereof by means of a guide, in particular a guide connector and in particular also a fastening flange fastened to the guide connector, and can be fixed or secured in a plurality of axial positions within an adjustment region by means of at least one fixing means, in particular a fixing screw which can be screwed in from the outside through the guide connector, as a result of which in particular the rear end of the supply tube projects out of the guide connector to a greater or lesser extent, and/or the axial position of the supply tube and therefore the axial length thereof, can be adjusted, in particular upstream of the fastening flange. A line, in particular hose line, for supplying the injection medium is preferably connected to the rear end of the supply tube, in particular via a connecting piece, wherein the connecting piece is preferably connected, preferably releasably, at the rear end of the supply tube, in particular is screwed or can be screwed to the supply tube by means of a screw connection by means of corresponding threads, and/or has a connector for connecting the line, in particular by means of a seal or sealing sleeve.

At least two injection media can preferably be injected simultaneously and/or in parallel or in an alternating manner, and/or at least one injection medium is a disinfectant, in particular a disinfectant produced on a biological basis which is not harmful to humans, preferably without alcohol and aldehyde additives, but with active compounds, which are generally recognized as safe for health, against viruses, bacteria, fungi, spores, legionellae, germs and other pathogens and harmful organisms, and/or at least one injection medium is an aroma medium which may have an alcohol content of up to 2%, preferably below 0.3%, and/or is biologically degradable and/or is produced from natural oils.

According to the invention, a disinfection and aroma distributor for disinfecting and distributing aroma is therefore (also) proposed, characterized by at least one feature or any combination of a plurality of features of the features described in the present application, including the claims, and/or characterized by at least one feature or any combination of a plurality of the following features:

that said disinfection and aroma distributor consists of one, two, three or more pressure containers, that the pressure containers may be constructed from stainless steel, synthetic material, metal, rubber, glass or plastic, that the pressure containers in which the media are placed are provided with one, two or more pressure and filling lines, that the pressure containers are operated, but do not have to be operated, with a level display, that one or more compressors are required in order to introduce the necessary air pressure into the pressure containers in order to be able to release the media, that the housings in which the pressure containers are connected and stored may consist of one or more chambers, that the media may also be released by means of steam, that the active compound may also be released by means of a nozzle or atomizer, that the filling lines lead into a channel or equipment chamber, that the fragrance and disinfecting media used may be composed of solid, liquid or gaseous substances, that the disinfection and aroma distributor may be retrofitted on installations which already exist, that the disinfection and aroma distributor may also be provided in newly constructed installations ex factory, that the pressure containers have at least two connections for a compressor, that the pressure containers may be manufactured in different sizes, that the pressure containers may be provided with a float in order to indicate the contents, that the various disinfection and fragrance media may be distributed by the air flow, that the various media can be controlled by one or more solenoid valves which are connected to one or more time relays, that one or more pressure capsules may be provided in order to switch the system on or off, that the filling of the media and containers may be controlled by means of an electric regulating system, that the media may be refilled by simple topping up, that the disinfection and aroma distributor may also be used only as an aroma distributor, that the disinfection and aroma distributor may also be used only for disinfecting, that the media may also be released through one or more hoses connected to the pressure containers by means of steam in the appliances or aeration channels, that the compressor or the plurality of compressors may also be installed in the housing at the same time, but do not have to be, that the canisters with which the pressure containers are filled may be stored in the housing at the same time, but do not have to be, that the housing in which the system is located may also be lockable, that the disinfection and aroma distributor may also suck up and release the media by means of one or more attached pumps, instead of the compressors, that by using pumps, the media may also be interchanged by replacing entire containers (canisters) in which the media are located, that the housing chambers may be provided with sound protection, but do not have to be, that an additional housing in which the electric regulating system is located may also be attached to the housing, that the containers are connected to the compressor or pumps by one or more pressure lines, that the system is installed in a housing, that the various media can be released in a regulated manner, that the disinfection and aroma distributor can also be used for other media.

BRIEF DESCRIPTION OF THE DRAWINGS

An exemplary embodiment of the invention is described in more detail below with reference to the appended figures, in which.

DETAILED DESCRIPTION OF THE PREFERRED EMBODIMENTS

Figure 1:
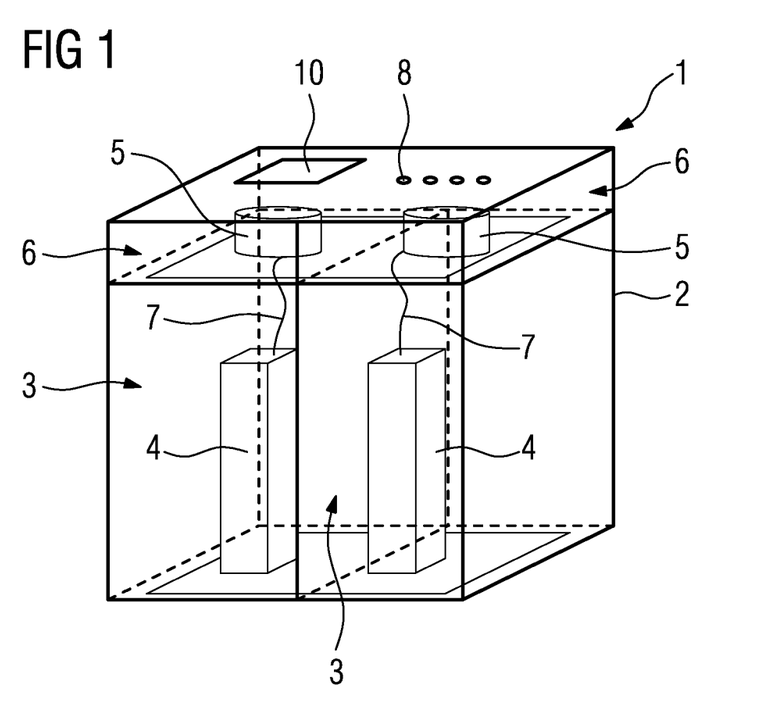
FIG. 1 shows schematically a perspective view of an injection device.

FIG. 1 shows a perspective view of an injection device 1. The injection device 1 comprises a housing 2 with two first compartments (or: chambers) 3 which may be separated by a partition, but do not have to be.

The two first compartments 3 are designed in the manner of a drawer and are designed such that they can be pulled out relative to the housing 2. Instead of the drawer, a first compartment 3 may also be designed as a box which is preferably closable with a flap. The drawer or the flap may be of closable design in order to prevent unauthorized access by a third party.

In the present case, an interchangeable container 4 is accommodated replaceably in each first compartment 3. Each interchangeable container 4 forms a storage container for an injection medium which can be injected by means of the injection device 1 into a line system (not shown in FIG. 1).

In the present case, the interchangeable containers 4 are pressure-operated interchangeable containers which can release the injection medium accommodated therein by being acted upon with positive pressure. The interchangeable containers 4 may be at least partially produced from stainless steel, synthetic material, metal, rubber, glass or plastic.

Each interchangeable container 4 is assigned a compressor 5 with which the interchangeable container 4, i.e. the injection medium, can be acted upon with positive pressure. The compressors 5 are arranged in separate second compartments 6 which are arranged above the respective first compartments 3 and are connected to the corresponding interchangeable containers 4 via pressure lines 7. The second compartments 6 are likewise designed in the manner of a drawer which can be pulled out. The division into first compartments 3 and second compartments 6 has the advantage in particular that damage to the components accommodated in the first compartments 3 and second compartments 6 during changing of an interchangeable container 4 or of a compressor 5 can be avoided. Apart therefrom, the removal of the interchangeable container 4 or of the compressor 5 is significantly simplified. The housing may comprise a fan, but at least a suitably designed aeration grill, in order to ensure sufficient cooling of the electronic components accommodated in said housing.

An interchangeable container 4 may have one or else two compressor connections which, in the operating position of the interchangeable containers 4, are preferably arranged facing the compressors 5. In the example of FIG. 1, the compressor connections would therefore be arranged at the top of the interchangeable containers 4. The same applies to pumps of the injection unit, which may be provided instead of compressors, with corresponding pump connections on the interchangeable containers. Furthermore, it lies within the scope of the invention for a plurality of compressors 5 to be arranged in a single second compartment 6 or for a plurality of interchangeable containers 4 to be able to be accommodated in a single first compartment 3. In particular, it is possible for only a first compartment 3 and/or only a second compartment 6 to be provided, which compartments may also optionally be designed in the manner of a drawer.

The connection between the interchangeable containers 4 and the compressors 5 and between further, preferably hose-like, connections between further components of the injection device 1 involves plug-in couplings and/or rapid-action couplings, insofar as is possible and applicable.

In the present exemplary embodiment, each interchangeable container 4 is accommodated in a separate first compartment 3. However, it is also conceivable if a plurality of interchangeable containers 4 are accommodated in a first compartment 3. The sizes and filling volumes of the interchangeable containers 4 may be identical or else different. The interchangeable containers may have a holding capacity or filling content of 1-50 liters, preferably 5-20 liters. Different injection media, such as disinfecting medium and aroma medium, may therefore be metered in, if appropriate in different quantities, and simultaneously released in parallel or else in an alternating manner.

Lines (not shown) lead from the interchangeable containers 4 and/or the compressors to an interface with a plurality of external connections 8. An injection head via which the injection medium can be injected into the line system may be connected to the external connections 8. Some of the external connections 8 may also be combined in the manner of a multiple plug such that, by production of just one connection with one injection head, a plurality of injection media can be injected via the same injection head.

Instead of or in combination with the compressors 5, one or more pumps may also be provided via which the injection medium can be conveyed at least out of the interchangeable containers 4.

The injection device 1 furthermore has a control system (not explicitly shown) with a user control panel 10 via which the injection device 1 can be controlled. The control system may be accommodated in a further compartment or in a housing or housing part of the injection device 1. The user control panel 10 may be designed in the manner of a desk, in particular a control console, on the second compartment or second compartments 6.

Figure 2:
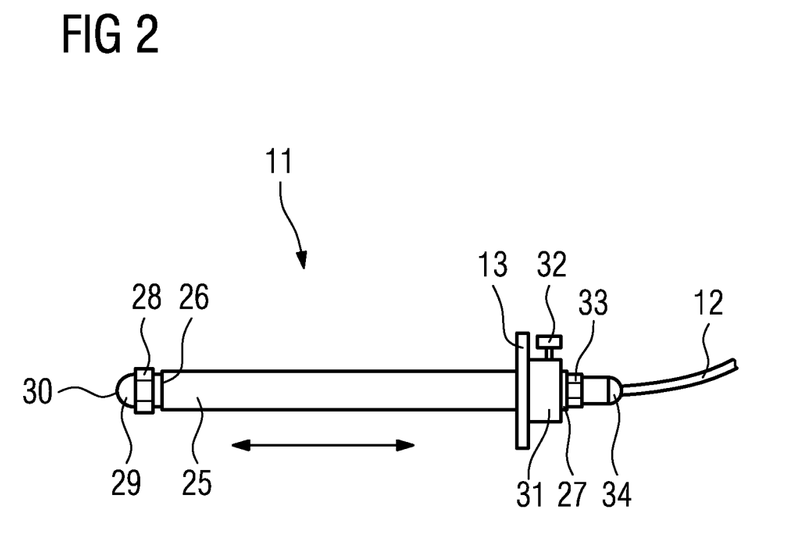
FIG. 2 shows an injection head.

FIG. 2 shows an injection head 11 of the injection device 1. The injection head can be connected to at least one of the compressors 5 (or pumps) or the interchangeable containers 4 via a line 12, preferably a hose line. The injection head 11 has a fastening flange 13 with which the injection head 11 may be fastened to a line system.

The length of the injection head 11 can be changed in the longitudinal direction thereof, this being indicated in FIG. 2 by means of a double arrow. The injection head may therefore be adapted to particular circumstances of the line system, such as diameter and the like.

The injection head 11 according to FIG. 2 preferably comprises a, for example, cylindrical supply tube 25 with a front end 26 and a rear end 27.

At its free end or the front end 26 of the supply tube 25, the injection head 11 has an injector nozzle 14, which is preferably a hollow conical nozzle. The injector nozzle 14 has a nozzle housing 30 which is dome-shaped or curved on the outside and has an internal, conically tapering channel (not visible) which leads into an outlet opening 30 of the injector nozzle 14 for the injection medium. The injector nozzle 14 furthermore has a screw connecting piece 28 with an external thread which is screwed into an internal thread at the front end 26 of the supply tube 25 and in particular has a polyhedron for the attachment of a spanner. This permits easy removability or interchangeability of the injector nozzle 14 from or on the supply tube 25. However, other releasable or else non-releasable fastening means for the injector nozzle 14 are also possible.

The supply tube 25 is guided axially along the longitudinal direction thereof by means of a guide connector 31 and a fastening flange 13, which is fastened to the guide connector 31, and is movable axially relative to said fastening flange and can be fixed in an axial position by means of a fixing screw 32 which is screwed in radially from the outside through the guide connector 31 and clamps the supply tube 25 from the outside. As a result, the rear end 27 of the supply tube 25 projects out of the guide connector 31 to a greater or lesser extent, and the axial position of the supply tube 25 and therefore the axial length thereof upstream of the fastening flange 13 can be adjusted or varied in the axial direction (indicated by the double arrow) in order to permit an optimum injection position for the injector nozzle 14. Instead of the fixing screw 32, other fixing means for fixing the supply tube 25 are also possible.

A line, in particular hose line 12, for supplying the injection medium is connected to the rear end 27 of the supply tube 25 via a connecting piece 33. The connecting piece 33 has an external thread (analogously to the screw connecting piece 28) which is screwed into an internal thread in the supply tube 25 at the rear end 27 thereof and preferably likewise has a polyhedron and a connector for connecting the line 12 by means of a seal or sealing sleeve 34.

Figure 3:
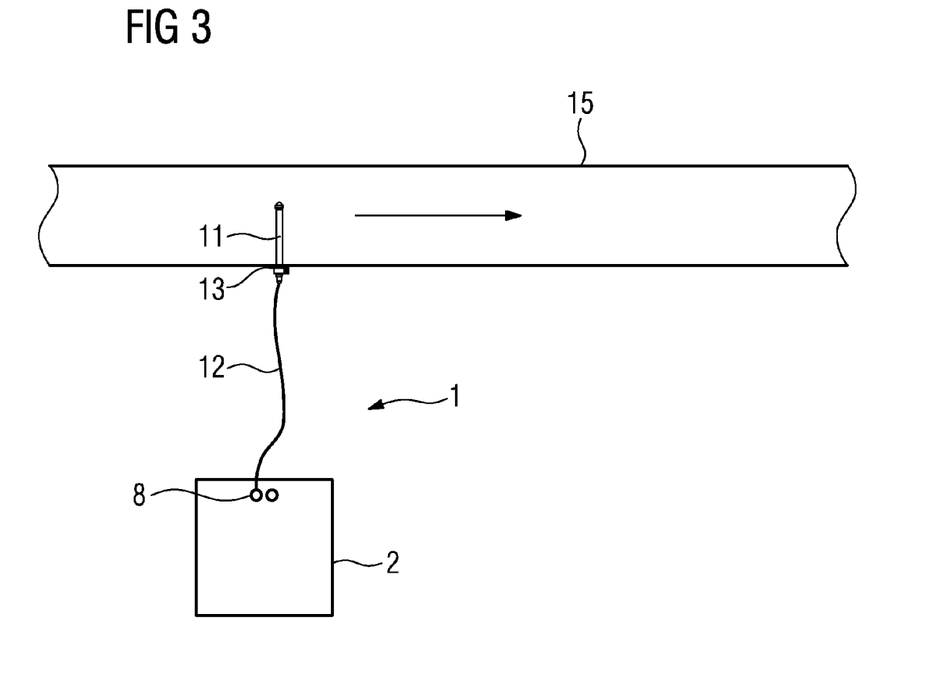
FIG. 3 shows schematically a line system with an injection device.

FIG. 3 shows schematically a line system 15 with an injection device 1 installed thereon. The compressor or the compressors 5 and the interchangeable container or the interchangeable containers 4 is or are connected to the injection head 11 via at least one line 12. The injection head 11 is fastened by the fastening flange 13 to an outer wall of the line system 15. The length of the injection head 11 is adjusted in such a manner that the injector nozzle 14 is arranged approximately centrally in the line system 15.

The function of the injection device 1 which is coupled to the line system 15 is as follows:

The line system 15, which may be a ventilation system, in particular an air conditioning system, may be supplied, depending on requirements, with the injection medium via the injection device 1. The injection medium may be supplied to disinfect the line system 15, to eliminate unpleasant odours or for other purposes, such as, for example, to enrich the medium conveyed in the line system with essentially any substances. In all cases, the injection device may be operated in the same manner.

In the present refinement, the respective compressor 5 generates a positive pressure of 1 to 6 bar, preferably of 3 to 4 bar, in the interchangeable container 4. The injection medium which is thereby acted upon with positive pressure can be injected via electronically controllable solenoid valves and ultimately via the injector nozzle 14 into the volumetric flow of the line system 15.

In particular for disinfection and aroma purposes, the injection medium or the injection media may be injected into the volumetric flow in the form of a gas and/or in the form of a liquid or solid aerosol. Use may be made here of steam, carburettor or air atomizing nozzles. Conical hollow nozzles, preferably with an integrated filter, are in particular suitable.

After the injection medium is injected, i.e. released, in the line system 15, the at least one injection medium may be distributed further by means of the flow in the line system 15. In this case, the flow in the line system 15 may be taken into consideration even as the injection medium is being injected, in order to optimally distribute the respective injection medium.

FIG. 3 is based on a flow directed from the left to the right in the line system 15, this being indicated by an arrow. Air flowing past the injection head 11 picks up the injection medium released by the injection head 11, this being indicated in FIG. 3 by means of a texture. The injected injection medium is distributed in the line system 15 and, if appropriate, into rooms coupled thereto by the flow in the line system 15.

The injection may be controlled by an electronic control system (not shown) which interacts with the user control panel 10. In this case, it is possible to control the injection as a function of sensors coupled to the line system, such as, for example, flow sensors, temperature sensors, pressure sensors and the like.

The control system can furthermore bring about temporal triggering of the injection device by, for example, the injection medium being injected for respectively predetermined periods of time at predetermined intervals. The intervals and periods of time may be selected as a function of the volumetric flow, the type of medium located in the line system 15, the temperature, the pressure or other parameters. In conjunction with the triggering, it is possible, for example, to inject the injection medium for 20 or 30 seconds in each case at intervals of 60 minutes. Other suitable variations in time for the injection of the injection medium are conceivable.

FIG. 3 shows just one injection head 11. It lies within the scope of the invention for the injection device 1 to have a plurality of injection heads 11 which are or can be connected to the line system 15. In this case, each injection head 11 may be coupled to one interchangeable container 4 in each case. This enables different injection media, such as disinfecting media, aroma media etc., to be injected in a separately controlled manner. However, it is also possible for one injection head 11 to be coupled to a plurality of interchangeable containers 4, and for the supply of the respective injection media to the injection head 11 to be controlled by means of valves, in particular solenoid valves. It is therefore clear that, with the injection device, essentially any injection media can be injected into the line system 15 in virtually any combination and mixture.

In order to improve the continuous operation of the injection device 1, it is possible for one or more level indicators to be provided, with which the respectively current level of the interchangeable container or interchangeable containers 4 is indicated. The level indicators may be provided on the interchangeable containers 4, for example in the form of floats or the like. As an alternative, one or more level indicators may also be provided on the injection device 1, preferably in such a manner that the respectively current levels are also visible from the outside whenever the housing 2 is closed. The level indicators may be integrated, for example, into the user control panel 10.

As FIG. 3 shows, the injection head 11 is connected via the line 12, which may be a hose connection and the like, to one of the external connections 8 with the use of a rapid-action coupling. The external connection 8 in turn is connected with the interconnection of lines, in particular hoses, valves and other elements for controlling the dispensing of injection medium, to one of the interchangeable containers 4. When the injection head 11 is connected, a, for example, liquid injection medium is injected by the corresponding injection medium, which is acted upon with positive pressure by the compressor 5, passing, by a valve opening up, via the line 12 to the injection head 11 where it is dispensed into the volumetric flow at the injector nozzle 14, preferably a hollow conical nozzle, in the form of a liquid aerosol because of the positive pressure. Gaseous or solid, for example pulverulent, injection media may correspondingly be injected or placed into the volumetric flow. It should be mentioned that the injection medium may also comprise a plurality of phases, such as, for example, in a suspension.

The length of the line 12 may essentially be selected as desired, at least insofar as the injection medium can still be satisfactorily injected, for example despite the pressure drop occurring in the line 12. It is therefore possible to guide the lines 12 which are connected to the injection heads 11 along the line system 15 to a common location at which the lines 12 can be connected to a single injection device 1 via the external connections 8. It is thereby possible to control the injection of injection medium for a multiplicity of injection sites of the line system 15 or else a plurality of different line systems centrally using the single injection device 1. Furthermore, it is possible to provide the injection device 1 and to connect it only as required, for example, if the line system 15 is only to be disinfected in a monthly cycle. In the meantime, the injection device 1 may be used elsewhere.

In order to prevent unauthorized access to the injection device 1, in particular to the interchangeable container 4, it can be provided to design the housing to be lockable. From this point of view, it is also advantageous if the user control panel 10 can be locked at the same time or latched or blocked by means of suitable measures, such as, for example, by access codes and the like.

A disinfectant which is not harmful to humans may be produced, for example, on a biological basis, preferably without alcohol and aldehyde additives. At any rate, the injection medium may comprise active compounds, which are generally recognized as safe for health, against viruses, bacteria, fungi, spores, legionellae, germs and other pathogens and harmful organisms. For example, the disinfectant sold by DeBeTek GmbH may be used.

If the injection medium is used for distributing aroma, said injection medium may have an alcohol content of up to 2%, preferably below 0.3%. The aroma medium is preferably biologically degradable and produced from natural oils.

Finally, the injection device 1, in particular the housing 2, in particular the respective second compartment 6, may have sound insulation such that the noise annoyance emanating from the injection device 1 during the operation thereof can be at least significantly reduced. This results in further spheres of use and use options for the injection device 1, in particular in noise-sensitive areas.

Figure 4:
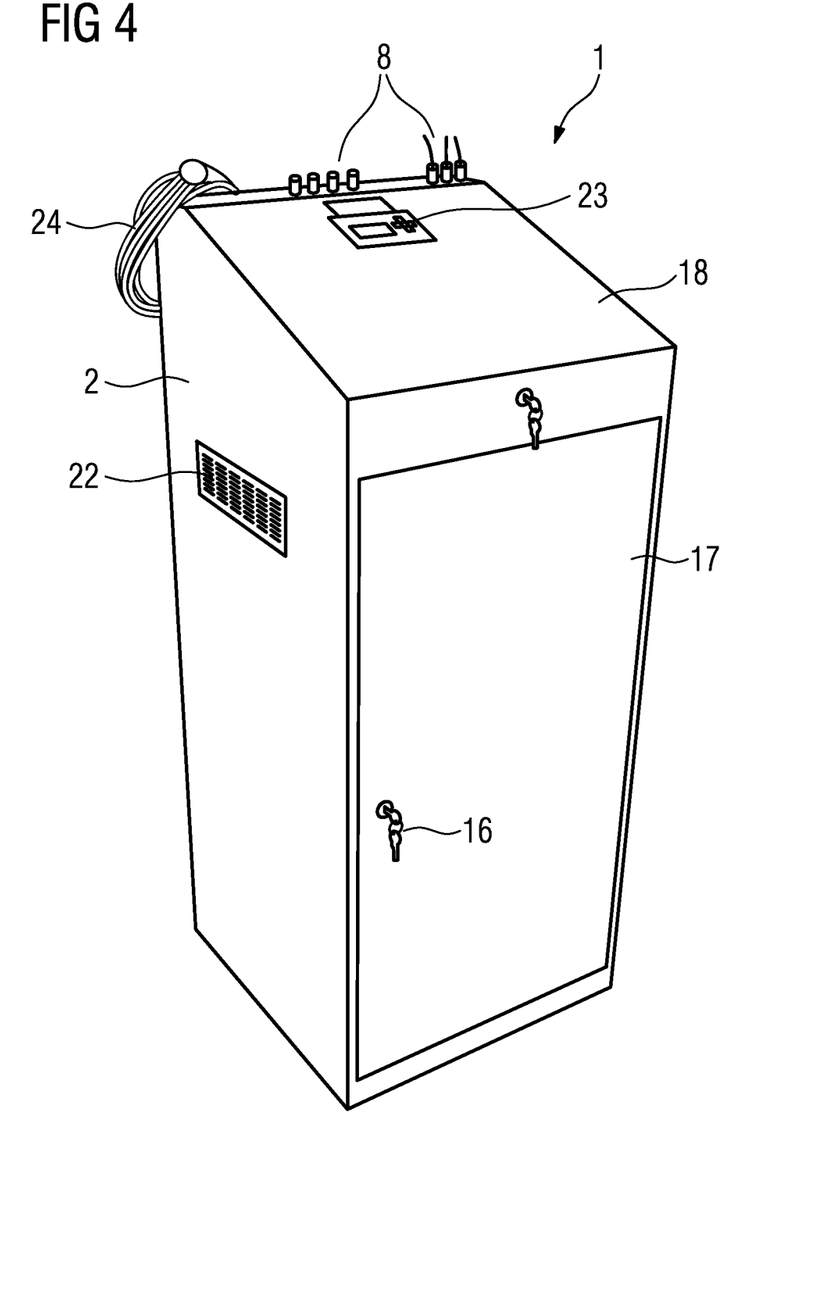
FIG. 4 shows a perspective outside view of the housing of an injection device.
Figure 5:
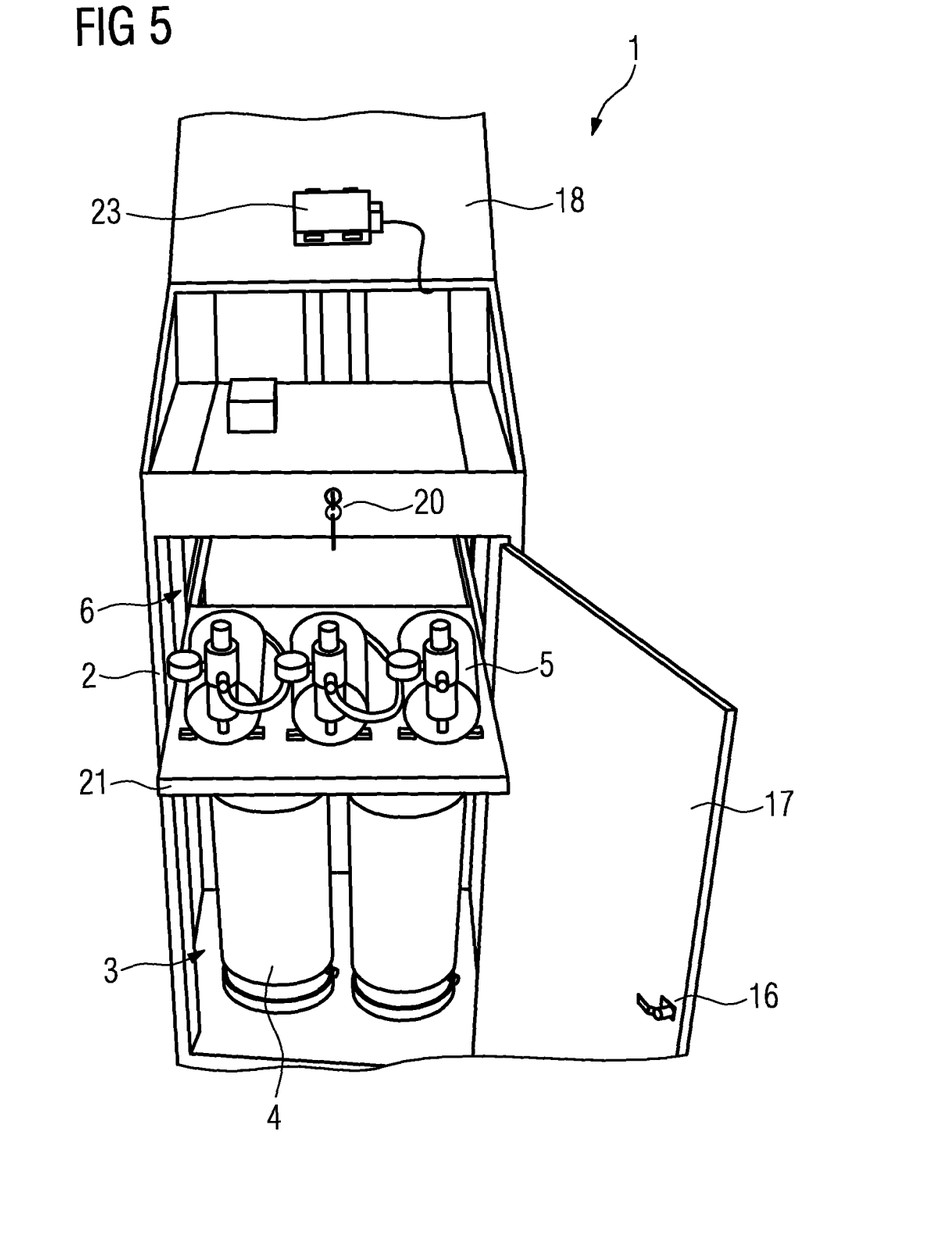
FIG. 5 shows a perspective view of the injection device according to FIG. 4 with the housing open.

FIG. 4 shows a perspective outside view of the housing 2 of an injection device 1. FIG. 5 shows a perspective view of the injection device 1 with the housing 2 open.

In the present case, the housing 2 is designed as an upright housing in the manner of a lectern. The housing 2 has a door 17 which is lockable by a key-lock system 16 and opens forwards in a rotating manner. The door 17 is attached laterally at an opening in the housing 2 via hinges and is therefore mounted rotatably, which can be seen more precisely in FIG. 5. The door 17 is designed to close the first compartment 3 and the second compartment 6, the key-lock system 16 giving rise to the option of preventing unauthorized access to the first compartment 3 and second compartment 6.

The housing 2 furthermore has a third compartment 19 which can be closed by a flap 18 and can serve, inter alia, as a storage compartment or to accommodate further electronic components. The third compartment 19 may be locked via a further key-lock system 20 so that unauthorized access to the third compartment 19 can be prevented. In the present case, the flap 18 is designed to be raised upwards and, in the closed state, slopes obliquely forwards, thus resulting in the lectern-like configuration of the housing 2. The third compartment 19 may alternatively be designed as a drawer which is preferably to be opened forwards.

As can be seen in FIG. 5, the compressors 5, if appropriate also other components, such as pumps, electronic components and the like, are arranged on a tray 21, which can be pulled out forwards, of the second compartment 6, FIG. 5 showing the pulled-out state of the tray. What is not shown but is nevertheless possible is that the first compartment 3 has a further tray which can be pulled out forwards and on which the interchangeable containers 4 can be accommodated. The tray which can be pulled out and, if appropriate, the further tray which can be pulled out permit simple replacement and simple maintenance of the respective components. Furthermore, when the trays are pulled out, hoses, lines, in particular the pressure line 7 and the like, may be connected in a simple manner.

To avoid a build up of heat when the housing 2 is closed, the latter has a cooling device. In the present example, the cooling device comprises at least one aeration grill 22 which, as in the present case, may be attached to a side wall of the housing 2. The aeration grill 22 permits removal of the waste heat generated by the components accommodated in the housing, in particular the compressors 5 and any electronic components. In an advantageous manner, more than one, in particular two, aeration grills 22 are provided in such a manner that a cooling airstream made possible by said aeration grills may act upon the components to be cooled and thereby protect the latter from overheating. If a sufficient cooling effect cannot be achieved by convection alone, the cooling device may furthermore have one or more fans with which a defined cooling airstream can be generated in the housing. As an alternative or in addition, the cooling device may comprise active cooling elements, such as evaporators or Peltier elements.

The cooling device should at any rate be configured in such a manner that at least overheating of the electronic components, such as the compressors 5, can be avoided. If required, the cooling device may also be configured in such a manner that the injection media accommodated in the interchangeable containers 4 can be cooled.

As is apparent from FIGS. 4 and 5, the flap 18 has a preferably digital display unit and/or control unit 23 integrated therein. The display unit and/or control unit 23 may comprise, for example, a preferably central control system or may be connected to such a control system such that at least the essential parameters and magnitudes may be displayed and/or adjusted. The control unit 23 may be designed, for example, in such a manner that essentially the entire operating mode of the injection device 1 can be retrieved and, if appropriate, programmed. The display unit and/or control unit 23 and/or, if appropriate, further switching and functional elements may be provided, as described, on the flap 18, or at other suitable locations in the housing and/or in the first compartment 3 to third compartment 19. For example, it would be possible to arrange the control unit 23 in the third compartment 19 such that said control unit would be protected against unauthorized access when the flap 18 is closed and locked.

As can furthermore be seen from FIG. 4, in the upper region of the flap 18, the housing 2 has external connections 8 to which, for example, lines 12 from injection heads 11 or other, for example electronic, components can be connected. The external connections 8 may be provided with securing devices which are intended to prevent unauthorized connection or removal of the lines 12 and the like.

In particular the injection device 1 which is described with regard to FIGS. 4 and 5 has proven to be a flexible appliance which can be installed with little outlay and in few steps, such as, for example, connection to a power supply via a mains cable 24 and connection of one or more injection heads 11 to the external connections 8.

Without restricting the general character, the invention can be characterized in particular by the following features:

- Pressure container with aroma-distributing substance and/or pressure container with disinfecting substance, both in liquid form.
- Compressed air connection to the pressure container, preferably at the top, the compressed air connection being connected to an associated compressor/or pumps for generating the compressed air, preferably via a hose, and the compressed air lying within a range of 1 bar to 6 bar (preferably operating pressure of 2 to 3 bar).
- Hollow conical nozzle with integrated filter on the wall of the air duct with a pressure capsule and valve for switching the ventilation and air conditioning system on and off upon starting said system up or shutting said system down.
- Special configuration of the injection nozzle with a nozzle tube which projects into the air duct and can be adjusted in length.
- The system may be equipped with one container to a plurality of containers, since the system can be expanded in a simple manner by means of rapid-action plug-in couplings—connectors.
- Plug-in couplings/rapid-action plug-in couplings are provided on the hoses for connection to the containers and to the nozzles.
- Containers/canisters may be manufactured in different sizes/filling contents, from 1 liter to up to 50 liters and more, preferably 5-20 liters, and fitted into the system.
- The pressure containers/canisters can be placed into the system in a variable number, from one up to a plurality of containers.
- Compact construction in a common housing in which the pressure containers are arranged on a lower level, the compressors/or pumps/and a control console or control system are provided on an upper level, wherein the two lower levels containing pressure containers/canister/compressors/pumps may be constructed to be movable out of the housing and back in again using a drawer which can be pulled out.
- Regulation of the metering in by means of solenoid valves and the control system in particular in such a manner that the substance/substances are sprayed in at certain time intervals for a certain treatment period. For example, for 20 seconds every 60 minutes, or else for 10 seconds every 20 minutes. Fixed time intervals which are set in advance and are determined empirically are therefore preferably set. However, the regulation may additionally also be specifically set/adjusted to the ventilation and air conditioning system.
- The desk in which the regulating/control system is located is lockable, as is also the other region on the lower levels.
- The appliance is constructed to be ready for plugging in; it merely has to be brought in situ, plugged into or connected to a power point/or switch cabinet and, with little outlay, the nozzles are provided in the channels by drilling as many nozzles as necessary (bore preferably 20 mm per nozzle) and attaching the solenoid valves, which are preferably attached to the outer duct just upstream of the nozzles.
- The disinfectant is generally recognized as safe and is a disinfectant which is used on a biological basis without alcohol (fire prevention) and without aldehyde and in the food industry; it eliminates viruses, bacteria, mould fungi, legionellae, germs and other organisms which may cause infectious illnesses (disinfection sold by DeBeTek GmbH/disinfection of ventilation and air conditioning systems).
- The fragrance medium is likewise generally recognized as safe, with an alcohol content of below 0.3% (no risk of fire) and is likewise biologically degradable; said fragrance medium is produced from natural oils and is obtainable in various fragrances; the fragrance is intended to be for well-being, and to be relaxing and concentration-enhancing (fragrance sold by DeBeTek GmbH/fragrance for ventilation and air conditioning systems).
- The system may also be used for other media, for example for greenhouses, in the sphere of plant protection agents, for promoting growth, and for other spheres of the food industry or for oils, lubricants, water and other liquid media.
- The system may also be constructed in such a manner that a tank having a large holding capacity may be connected to the system.
- The system may be operated in a permanent operating position, at various time intervals or as desired.
- The system reliably disinfects not only air supply and exhaust systems/ducts but also the appliance chambers in the ventilation and air conditioning system, the air outlets and the associated surfaces in the premises; tests have revealed that, in the case of KBE units of 100 and more, up to 100% of the surfaces were disinfected.

Owing to the modular construction, different containers/substances can be combined or can be connected to the same nozzles; furthermore, multiple plugs enable connection to a plurality of ventilation and air conditioning systems/ducts.

The containers can easily be refilled or else simply be replaced or interchanged; for the refilling all that needs to be done is for the closure attached at the top to be opened, and the system emits a signal shortly before the next refilling is due.

A fan and an air grill are attached to the compact housing in order to protect the system from overheating at higher temperatures.

The system is regulated via pressure capsules or timers, if desired, or permanently via distribution of electricity at the switch cabinet.

The system may also be operated via simply either interchangeable or refillable canisters instead of by pressure containers.

The appliance may take on a plurality of functions simultaneously, in an alternating manner (fragrance/disinfection/oil/plant protection agents, etc.) or just one medium may be released and operated.

The appliance is intended to be used in a preventative manner to protect against infectious illnesses and to permit a safe environment for humans and animals.

LIST OF REFERENCE NUMBERS

1 Injection device
2 Housing
3 First compartment
4 Interchangeable container
5 Compressor
6 Second compartment
7 Pressure line
8 External connection
9 Control system
10 User control panel
11 Injection head
12 Line
13 Fastening flange
14 Injector nozzle
15 Line system
16 Key-lock system
17 Door
18 Flap
19 Third compartment
20 Further key-lock system
21 Tray
22 Aeration grill
23 Control unit
24 Mains cable
25 Supply tube
26 Front end
27 Rear end
28 Screw connecting piece
29 Nozzle housing
30 Nozzle outlet opening
31 Guide connector
32 Fixing screw
33 Connecting piece
34 Seal

I claim:

1. An injection device designed for injecting at least one injection medium into a volumetric flow of a line system of a ventilation system or air conditioning system, the injection device comprising:
    at least one container containing the at least one injection medium, the at least one injection medium comprising a disinfectant;
    at least one injection head in fluid communication with the at least one container, the at least one injection head being positionable to extend at least partially into the flow path of the line system, whereby the at least one injection medium can be selectively injected into the line system so that the at least one injection medium is distributed in the line system and into one or more rooms connected to the line system;
    at least one pump and/or compressor adapted to inject the at least one injection medium into the volumetric flow, via the at least one injection head; and
    a trigger device adapted for triggering the injection of the at least one injection medium in accordance with predefined time intervals.

2. The injection device according to claim 1, wherein each injection medium is accommodated in a separate container, preferably pressure-operated interchangeable container, and wherein each interchangeable container is preferably accommodated in a separate first compartment of a housing.

3. The injection device according to claim 1, further comprising:
    at least one level display for displaying the level of at least one interchangeable container containing the at least one injection medium; and/or
    a display; and/or
    a control unit preferably comprising a control system or that is connected to a control system and is intended for displaying and/or for adjusting operating parameters of the injection device.

4. The injection device according to claim 1, further comprising:
    a housing with:
        at least one first compartment set up to accommodate at least one injection medium, and
        at least one second compartment spatially separated or distinguishable from the first compartment;
        wherein at least one of the two compartments, preferably both the compartments, has or have at least one injection unit for injecting at least one of the at least one injection medium into the volumetric flow or the volume.

5. The injection device according to claim 4, wherein:
    the at least one first compartment is arranged spatially below the at least one second compartment; and/or
    the at least one first compartment and/or the at least one second compartment is designed to be movable relative to the housing in the manner of a drawer, wherein preferably at least one third compartment is provided, in particular for accommodating electronic components, wherein the injection device preferably comprises:
        a cooling device preferably comprising one or more aeration slots, and/or
        at least one aeration grill, and/or
        at least one fan for cooling components accommodated in the first compartment to the third compartment and/or in the housing of the injection device.

6. The injection device according claim 1, wherein:
the injection device is designed to inject the at least one injection medium into the volumetric flow at a positive pressure of 1-6 bar, preferably of 2-3 bar, preferably with the use of solenoids; and/or
the at least one injection device is connected to one or more interchangeable containers, and/or wherein the at least one interchangeable container can connect the at least one injection device and/or the at least one injection head to one another by means of plug-in couplings and/or rapid-action couplings.

7. The injection device according to claim 1, wherein the at least one injection head is positionable to extend at least partially into the flow path of the line system, preferably transversely with respect to the direction of flow, and is intended for injecting at least one of the injection media into the line system,
wherein the injection head is adjustable preferably in the length thereof located within the line system and/or runs in the direction transversely with respect to the direction of flow and/or in the axial position thereof within the line system.

8. The injection device according to claim 7, wherein:
the injection head is designed to place the at least one injection medium in the form of a gas, in the form of a liquid and/or solid aerosol, into the volumetric flow, and/or
the injection head comprises an injector nozzle, in particular a hollow cone nozzle, in particular with a filter, in particular an integrated filter,
wherein the injector nozzle in particular has a nozzle housing that is dome-shaped or curved on the outside and has an internal channel that tapers conically and leads into an outlet opening of the injector nozzle for the injection medium.

9. The injection device according to claim 7,
wherein the injection head has a supply tube with a front end and a rear end,
wherein the injector nozzle is preferably connected, preferably releasably, to the front end of the supply tube, in particular by means of a screw connection piece that is or can be screwed to the supply tube by means of corresponding threads, and/or
wherein the supply tube is guided, preferably axially, along the longitudinal direction thereof by means of a guide, in particular a guide connector and in particular also a fastening flange fastened to the guide connector, and is movable axially relative to said fastening flange and can be fixed or secured in a plurality of axial positions by means of at least one fixing means, in particular a fixing screw, the at least one fixing means being screwed in from the outside through the guide connector, whereby the rear end of the supply tube projects out of the guide connector to a greater or lesser extent and/or the axial position of the supply tube and therefore the axial length thereof, can be adjusted, in particular upstream of the fastening flange, and/or
wherein a line, in particular hose line, for supplying the injection medium is preferably connected to the rear end of the supply tube, in particular via a connecting piece,
wherein the connecting piece is preferably connected, preferably releasably, to the rear end of the supply tube, is or can be screwed to the supply tube in particular by means of a screw connection by means of corresponding threads and/or has a connector for connecting the line, in particular by means of a seal or sealing sleeve.

10. The injection device according to claim 1, in which:
at least two injection media can be injected simultaneously and/or in parallel or in an alternating manner, and/or
at least one injection medium is:
a disinfectant, in particular a disinfectant produced on a biological basis that is not harmful to humans, preferably without alcohol and aldehyde additives, but with active compounds that are generally recognized as safe, against viruses, bacteria, fungi, spores, legionellae, germs and other pathogens and harmful organisms, and/or
an aroma medium having an alcohol content of up to 2%, preferably below 0.3%, and/or
is biologically degradable and/or is produced from natural oils.

11. A ventilation or air conditioning system comprising:
a line system having a volumetric flow;
an injection device designed for injecting at least one injection medium into the volumetric flow of the line system, the injection device comprising:
at least one container containing the at least one injection medium, the at least one injection medium comprising a disinfectant;
at least one injection head in fluid communication with the at least one container, the at least one injection head being positionable to extend at least partially into the flow path of the line system, whereby the at least one injection medium can be selectively injected into the line system so that the at least one injection medium is distributed in the line system and into one or more rooms connected to the line system;
at least one pump and/or compressor adapted to inject the at least one injection medium into the volumetric flow, via the at least one injection head; and
a trigger device adapted for triggering the injection of the at least one injection medium in accordance with predefined time intervals.

12. A method for disinfecting a line system of a ventilation or air conditioning system, the method comprising:
providing an injection device designed for injecting at least one injection medium into a volumetric flow of the line system, the injection device comprising:
at least one container containing the at least one injection medium, the at least one injection medium comprising a disinfectant;
at least one injection head in fluid communication with the at least one container; and
at least one pump and/or compressor adapted to inject the at least one injection medium into the volumetric flow, via the at least one injection head;
positioning the at least one injection head to extend at least partially into the volumetric flow of the line system;
injecting the at least one injection medium into the volumetric flow of a line system in accordance with predefined time intervals, whereby the at least one injection medium is distributed in the line system to disinfect the line system.

* * * * *